United States Patent [19]

Nagata et al.

[11] 4,025,553

[45] May 24, 1977

[54] PRODUCTION OF O-HYDROXYBENZYL ALCOHOLS

[75] Inventors: Wataru Nagata, Nishinomiya; Kyo Okada, Osaka; Hiroshi Itazaki, Takarazuka; Tsutomu Aoki, Takatsuki, all of Japan

[73] Assignee: Shionogi & Co., Ltd., Osaka, Japan

[22] Filed: Sept. 23, 1975

[21] Appl. No.: 615,884

[30] Foreign Application Priority Data

Oct. 9, 1974 Japan ............................. 49-116469

[52] U.S. Cl. ...................... 260/521 R; 260/296 P; 260/622 P; 260/619 F; 260/296 B; 260/623 R; 260/624 R; 260/297 R; 260/475 SC; 260/462 R; 260/462 C; 260/465 D; 260/465 F; 260/471 R; 260/473 R; 260/473 F; 260/473 A; 260/473 G; 260/473 S; 260/475 R; 260/475 FR; 260/475 PN; 260/475 F; 260/520 E; 260/520 B; 260/520 D; 260/520 R; 260/521 P; 260/521 H; 260/521 B; 260/612 R; 260/612 D; 260/613 R; 260/613 D; 260/619 R; 260/620; 260/621 K; 260/622 R

[51] Int. Cl.² .................... C07C 7/00; C07C 37/00; C07C 51/00; C07F 5/04

[58] Field of Search ........ 260/521 R, 521 B, 521 H, 260/521 P, 621 K, 622 R, 622 P, 620, 623 R, 624 R, 619 R, 613 R, 613 D, 520 C, 520 D, 520 E, 488 CD, 465 D, 465 F, 465 G, 465 H, 462 C, 296 P, 296 B, 297 R, 471 R, 473 R, 473 F, 473 A, 473 G, 473 S, 475 R, 475 SC, 475 FR, 475 PN, 475 F, 520 R, 520 B, 612 R, 612 D, 619 F

[56] References Cited

UNITED STATES PATENTS 3,479,294  11/1969  Weck .............................. 260/621 K

FOREIGN PATENTS OR APPLICATIONS 630,052  3/1963  Belgium ......................... 260/621 K Primary Examiner—Norman Morgenstern
Attorney, Agent, or Firm—Wenderoth, Lind & Ponack

[57] ABSTRACT

A novel process for producing o-hydroxybenzyl alcohols useful as raw materials or intermediates in chemical or pharmaceutical industries, which comprises reacting phenols or naphthols with aromatic boronic acids and aldehydes in the presence of organic carboxylic acids, followed by degradation of the cyclic ester intermediates.

7 Claims, No Drawings

PRODUCTION OF O-HYDROXYBENZYL ALCOHOLS

The present invention relates to a novel chemical process for producing o-hydroxybenzyl alcohols by introducing 1-hydroxyalkyl or α-hydroxyaralkyl at the ortho position of phenols.

Several processes for o-alkylation of phenols as well as processes for reducing the formyl or carboxyl at the α-position of phenols to benzyl alcohols are widely noted [for example, Rec. Trav. Chim. 79, 825 (1960); Jap. Pat. Pub. No. 39-17518 (1964); Brit. Pat. No. 774,696]; these processes, however, are disadvantageous in that the field to which they are applicable is limited, they require troublesome procedures, and they result in a poor yield of final product; in fact, there is no appreciable process for producing o-hydroxybenzyl alcohols, which is relatively inexpensive and widely applicable.

The present inventors recognized the fact that o-hydroxybenzyl alcohols involve a wide variety of raw materials useful in chemical or pharmaceutical industries and as intermediates in the preparation of important naturally occurring compounds, including saligenin (or saligenol), and undertook an investigation in order to develop a new process which would be widely applicable and relatively inexpensive. The present invention was thus brought to completion.

The gist of the present invention resides in reacting an optionally substituted or unsubstituted phenol or naphthol with an aromatic boronic acid and an aldehyde in the presence of an organic carboxylic acid, and then degrading the product to introduce 1-hydroxyalkyl or α-hydroxyaralkyl at the ortho position of the hydroxy of the phenol or naphthol. One of the advantages of it is that this process is widely applicable to o-hydroxybenzylation of phenols. In order to make the invention easily understood a simple case is exemplified by the following reaction sequence in which phenol as the starting compound and benzeneboronic acid as the aromatic boronic acid are used.

of 7–10 carbon atoms (those containing the aforementioned aralkyls), halogens (chlorine, bromine, iodine), carboxyl or alkoxycarbonyl of 2–6 carbon atoms (e.g. methoxycarbonyl, ethoxycarbonyl), nitro, cyano, and the like. The aforementioned alkyls, aryls, aralkyls, alkoxys, aryloxys, and aralkoxys may be substituted by an additional alkyl, aryl, aralkyl, alkoxy, aryloxy, aralkoxy, halogen, carboxyl or alkoxycarbonyl, nitro, or cyano as defined above. The phenols may be condensed with a benzene ring; the starting compounds in this sense mean naphthols. The naphthols may be 1-naphthols or 2-naphthols, and the aforementioned substituents may be located on the ring unsubstituted by the hydroxy. With regard to both the phenols and naphthols, there is no limitation on the location of the aforementioned substituents, but the case in which the ortho position of the phenolic hydroxy is occupied by a certain substituent is naturally excluded.

The aromatic boronic acid reacted with the above compounds basically means benzeneboronic acid, and in addition to this acid other boronic acids having aromatic groups other than phenyl (e.g. tolyl, xylyl, methoxyphenyl, nitrophenyl, pyridyl) and their esters or anhydrides may be utilized in the same manner.

The aldehydes simultaneously used mean aliphatic and aromatic aldehydes exemplified by formaldehyde, acetaldehyde, propionaldehyde, butyraldehyde, benzaldehyde, phenylacetaldehyde, and the like. These compounds may be substituted by non-reactive substituents as mentioned above, or may be such derivatives as paraldehydes.

The organic carboxylic acid added to the reaction medium acts as a sort of catalyst, and any type of acid may be used as far as it has a carboxyl group. Preferable examples of the acids are lower alkanoic acids such as acetic acid, propionic acid, butyric acid, and the like. If required, a strong acid such as trichloroacetic acid may be used.

The reaction is carried out in an anhydrous solvent containing a catalytic amount (0.1–1.0 mole) of organic carboxylic acid under heating (refluxing temperature of the solvent used) while eliminating the water

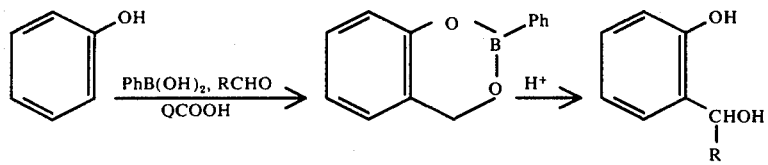

wherein R represents a hydrogen, alkyl of 1–5 carbon atoms, aryl of 6–10 carbon atoms or aralkyl of 7–10 carbon atoms, and Q represents an alkyl of 1–5 carbon atoms which may be substituted by aryls, alkoxys, aralkoxys or halogens as defined below).

The starting compounds of the invention involve basically the phenol as illustrated in the above formula, which may be substituted by preferably no more than four substituents on the phenyl of the starting phenol as far as it does not substantially disturb the reaction progress. Representative of such type of substituents are alkyls of 1–5 carbon atoms (e.g. methyl, ethyl, propyl, isopropyl, butyl, amyl), aryls of 6–10 carbon atoms (e.g. phenyl, tolyl, xylyl, naphthyl, pyridyl), aralkyls of 7–10 carbon atoms (e.g. benzyl, phenethyl), alkoxys of 1–5 carbon atoms (those containing the aforementioned alkyls), aryloxys of 6–10 carbon atoms (those containing the aforementioned aryls), aralkoxys produced, using an aromatic boronic acid and an aldehyde both in slightly excess amount (1.0–1.6 mole) to the phenol or naphthol. As for the reaction solvent, aprotic organic solvents, particularly, benzene, toluene, or xylene, may preferably be used in order to eliminate water produced with progress of the reaction as azeotrope. For the purpose of effective elimination of water, it is also possible to use a drying agent, for example, silica gel, molecular sieve (trade name, Linde Co.), anhydrous calcium sulfate, anhydrous calcium chloride, anhydrous magnesium sulfate. The reaction time depends upon the activity of the starting compound, aromatic boronic acid, aldehyde and organic carboxylic acid, the reaction temperature and the solvent used, and the reaction usually requires approximately 2–48 hours for the reaction completion.

The resulting intermediates are cyclic esters formed between the objective o-hydroxybenzyl alcohol and the aromatic boronic acid, of which the purification is not necessarily required, and may be subjected to subsequent degradation. The degradation is carried out in an alkaline or slightly acidic condition using a hydrogen ion donor (proton) at a temperature from room temperature to 100° C for a period of 1–10 hours. The most convenient method is hydrolysis or alcoholysis, and the purpose is attained well even in a neutral condition depending on the property of intermediate (for example, referred to Example 2). The alcoholysis may be effected by means of a lower alcohol of 1–5 carbon atoms such as methanol, ethanol, propanol, or the like. In this invention, however, polyalcohols of 2–3 carbon atoms such as ethylene glycol, propylene glycol, trimethylene glycol, glycerin, and the like are preferably used in the alcoholysis since the aromatic boronic acids and glycols form stable cyclic esters. The degradation conducted under acidic conditions is readily accompanied by side-reactions, and should accordingly be carried out in a slightly acidic medium; it is appropriate to use as the acid, an organic carboxylic acid such as acetic acid, propionic acid, and the like which act as hydrogen ion donors.

The reactions proceed very well and selectively to give the objective o-hydroxybenzyl alcohols in approximately 90% yield, and in some cases in quantitative yield.

As mentioned above, the o-hydroxybenzyl alcohols involve a wide variety of industrially important compounds including saligenin, and may be utilized particularly as intermediates in the preparation of o-hydroxymethylphenylacetic acids useful as plant growth regulators or protoberberine alkaloids useful as medicines or animal drugs. The present invention, accordingly, provides a novel industrial process for producing industrially useful o-hydroxybenzyl alcohols easily and in high yield.

The invention will be explained by the following examples which are not intended as a limitation thereof.

EXAMPLE 1

To a solution of 1.882 g (0.02 mole) of phenol, 2.439 g (0.02 mole) of benzeneboronic acid and 148 mg (2 mmole) of propionic acid in 50 ml of anhydrous benzene is added 1.0 g of paraformaldehyde under stirring and refluxing while removing the water as azeotrope. At 2 hours intervals, each 0.5 g of paraformaldehyde is added thereto, and after the lapse of 4 hours, an additional 0.488 g (4 mmole) of benzeneboronic acid is added, during which time the removal of water as azeotrope is continued. The reaction requires a total of 10 hours for the disappearance of phenol (checked by TLC). The reaction mixture is poured into a mixture of methylene chloride-water, the paraformaldehyde remaining unchanged is filtered off, and the filtrate is extracted with methylene chloride. The extract is washed with water, dried and evaporated to give 4.114 g (97.76% yield) of benzeneboronic acid cyclic ester of o-hydroxybenzyl alcohol. This is recrystallized from petroleum ether to give pure crystals having mp. 36°–38° C. NMR (CDCl$_3$) δ: 5.15 (2H, singlet), 7.07 (4H, multiplet), 7.43 (3H, multiplet), 8.00 (2H, multiplet) ppm. Anal. Calcd. for C$_{13}$H$_{11}$O$_2$B: C, 74.33; H, 5.28 (%). Found: C, 74.49; H, 5.34 (%).

The above cyclic ester (4.20 g; 0.02 mole) is dissolved in 150 ml of trimethylene glycol together with 120 mg of acetic acid, and the mixture is stirred at room temperature for 6 hours. The reaction mixture is extracted with ether, and the extract is washed well with water, dried and evaporated to dryness. The residue is crystallized from petroleum ether to give 2.107 g (84.86% yield) of saligenol (mp. 86°–87° C).

EXAMPLE 2

11.0 g of 3-hydroxy-4-methoxyphenylacetic acid is dissolved in 550 ml of benzene and refluxed to remove water as azeotrope. Then, 14.0 g of benzeneboronic acid is added thereto, and refluxed for approximately 1 hour while removing the water produced. (In this reaction, the starting phenylacetic acid works as the carboxylic acid catalyst) At 2–3 hour intervals, each 2–3 g of paraformaldehyde is added while continuing the removal of water, and after the lapse of 9 hours an additional 1.0 g of benzeneboronic acid is added thereto. The reaction is completed within a period of 20 hours, and the solvent is completely distilled off under reduced pressure. The crystalline residue after addition of 150 ml of water is kept on an oil bath at 90°–100° C for 1.5 hours under stirring. The reaction mixture is cooled to room temperature, and the precipitated crystals are collected and recrystallized from acetone-ether to give 9.70 g (83% yield) of 3-hydroxy-2-hydroxymethyl-4-methoxyphenylacetic acid as the δ-lactone having mp. 183°–185° C. IR $\nu_{max}^{CHCl_3}$ 3540, 1740, 1600, 1277, 1030, 983cm$^{-1}$. NMR (d$_6$-DMSO) δ 3.80 (3H, singlet), 3.65 (2H, singlet), 5.32 (2H, singlet), 6.70, 6.90 (AB quartet, J = 8.0 Hz), 8.07 (1H, singlet) ppm. Anal. Aclcd. for C$_{10}$H$_{10}$O$_4$: C, 61.85; H, 5.19 (%). Found: C, 61.70; H, 5.17 (%).

EXAMPLE 3

To a solution of 1.286 g of 4-chlorophenol and 1.219 g of benzeneboronic acid in 30 ml of anhydrous benzene is added 0.36 g of propionic acid, and the mixture is refluxed with stirring. Then, 1.0 g of paraformaldehyde is added thereto, and the refluxing is continued while removing the water produced as azeotrope. At 2–3 hours intervals, each 0.5 g of paraformaldehyde is added, and after the lapse of 9 hours, an additional 0.244 g of benzeneboronic acid is added. The refluxing is continued for a total of 15 hours. The reaction mixture is poured into a mixture of methylene chloride and water, and the precipitated paraformaldehyde is removed by filtration. The filtrate is extracted with methylene chloride, and the extract is washed with water, dried and evaporated to dryness. The residue is crystallized from petroleum ether to give 2.209 g (90.35% yield) of the cyclic ester of 2-hydroxy-5-chlorobenzyl alcohol with benzeneboronic acid having mp. 101°–102° C. NMR (CDCl$_3$) δ 5.13 (2H, singlet), 7.01 (3H, multiplet), 7.40 (3H, multiplet), 7.97 (2H, multiplet) ppm.

This cyclic ester is degraded in ethylene glycol to give 2-hydroxy-5-chlorobenzyl alcohol mp. 92°–93° C) in quantitative yield.

EXAMPLE 4–15

The following reactions are carried out in the same manner as in Example 1. The yield described indicates that of the cyclic ester of benzeneboronic acid; the yield of the degradation step is approximately quantitative (90% or more). Unless otherwise mentioned, paraformaldehyde as an aldehyde, propionic acid as a carboxylic acid, and benzene as a solvent are employed, and the reaction time is a period of 3–30 hours.

2-Methylphenol (o-cresol) gives the ester in 88% yield, which on degradation gives 2-hydroxy-3-methylbenzyl alcohol.

3-Methylphenol (m-cresol) gives the ester in 94% yield, which on degradation gives a 1:1 mixture of 2-hydroxy-4-methylbenzyl alcohol and 2-hydroxy-6-methylbenzyl alcohol.

4-Methylphenol (p-cresol) gives the ester in 97% yield, which on degradation gives 2-hydroxy-5-methylbenzyl alcohol.

2-Chlorophenol gives the ester in 38% yield (essentially in 90% or more yield because the starting compound is recovered quantitatively, hereinafter referred to as complete recovery), which on degradation gives 2-hydroxy-3-chlorobenzyl alcohol.

3-Methoxyphenol gives the ester in 99% yield, which on degradation gives a 1:1 mixture of 2-hydroxy-4-methoxybenzyl alcohol and 2-hydroxy-6-methoxybenzyl alcohol.

4-Methoxycarbonylphenol gives the ester in 37% yield, which on degradation gives 2-hydroxy-5-methoxycarbonylphenol.

1-Naphthol gives the ester in 90% yield, which on degradation gives 1-hydroxy-2-naphthylmethanol.

Naphthol gives the ester in 96% yield, which on degradation gives 2-hydroxy-1-naphthylmethanol.

The use of phenol and chloral gives the ester in 40% yield, which on degradation gives 2-hydroxy-α-trichloromethylbenzyl alcohol.

The use of phenol and hexanol gives the ester in 82% yield, which on degradation gives 2-hydroxy-α-pentylbenzyl alcohol.

The use of phenol and benzaldehyde in the presence of trichloroacetic acid gives the ester in 47% yield (complete recovery), which on degradation gives 2-hydroxy-α-phenylbenzyl alcohol.

The use of phenol and 4-nitrobenzaldehyde gives the ester in 20% yield (complete recovery), which on degradation gives 2-hydroxy-α-(4-nitrophenyl)-benzyl alcohol.

We claim:

1. A process for producing o-hydroxybenzyl alcohols which comprises reacting (1) a phenol or naphthol selected from the group consisting of phenol, naphthol and phenol and naphthol having a free ortho-position and containing up to 4 substituent groups selected from the group consisting of alkyl of 1–5 carbon atoms, aryl of 6–10 carbon atoms, pyridyl, aralkyl of 7–10 carbon atoms, alkoxy of 1–5 carbon atoms, aryloxy or 6–10 carbon atoms, pyridyloxy, aralkoxy of 7–10 carbon atoms, halogen, carboxy, alkoxycarbonyl of 2–6 carbon atoms, nitro and cyano, said alkyl, aryl, pyridyl, aralkyl, alkoxy, aryloxy, pyridyloxy and aralkoxy groups being unsubstituted or substituted by alkyl, aryl, pyridyl, aralkyl, alkoxy, aryloxy, pyridyloxy, aralkoxy, halogen, carboxy, alkoxycarbonyl, nitro or cyano as defined above, with (2) an aromatic boronic acid selected from the group consisting of phenyl, tolyl, xylyl, methoxyphenyl, nitrophenyl and pyridyl boronic acids and their corresponding anhydrides and esters and (3) an aldehyde of the formula R—CHO where R is hydrogen, alkyl of 1–5 carbon atoms, aryl of 6–10 carbon atoms, or aralkyl of 7–10 carbon atoms in the presence of (4) a catalytic amount of an alkanoic acid of 2–6 carbon atoms, the alkyl group of which may be substituted by aryl of 6–10 carbon atoms, pyridyl, alkoxy or 1–5 carbon atoms, aralkoxy of 7–10 carbon atoms or halogen in (5) an anhydrous aprotic organic solvent, under reflux conditions with elimination of water as said water is formed, to produce a cyclic boronic acid ester, and degrading said cyclic boronic acid ester under alkaline or slightly acid conditions using a hydrogen ion doner.

2. A process as claimed in claim 1, wherein the reactant (1) is phenol or the substituted phenol, and degradation of the cyclic boronic acid ester is carried out by acid hydrolysis or alcoholysis.

3. A process as claimed in claim 2, wherein the aldehyde is selected from the group consisting of paraformaldehyde, acetaldehyde, propionaldehyde, benzaldehyde, and phenylacetaldehyde.

4. A process as claimed in claim 2, wherein the aromatic boronic acid is phenylboronic 5. A process claimed in claim 2, wherein the alkanoic acid is selected from the group consisting of acetic acid, propionic acid, and butyric acid.

6. A process for producing saligenol which comprises reacting phenol with phenylboronic acid and paraformaldehyde in the presence of a catalytic amount of propionic acid in benzene under reflux conditions with elimination of water as said water is formed, and subjecting the resultant cyclic boronic acid ester to acid hydrolysis to degrade said ester.

7. A process for producing 3-hydroxy-2-hydroxymethyl-4-methoxyphenylacetic acid which comprises reacting 3-hydroxy-4-methoxyphenylacetic acid with phenylboronic acid and paraformaldehyde in benzene under reflux conditions with elimination of water as said water is formed, and subjecting the resultant cyclic boronic acid ester to hydrolysis in water at 90°–100° C under alkaline or slightly acidic conditions.

* * * * *